United States Patent [19]

Stöcker et al.

[11] Patent Number: 5,770,457
[45] Date of Patent: Jun. 23, 1998

[54] RAPID ONESIDE SINGLE TARGETING (ROST) IMMUNOASSAY METHOD

[75] Inventors: Ronald Helmut Stöcker, Monheim; Margit Doth, Krefeld, both of Germany

[73] Assignee: Bayer Aktiengesellschaft, Leverkusen, Germany

[21] Appl. No.: 737,901

[22] PCT Filed: May 15, 1995

[86] PCT No.: PCT/EP95/01829

§ 371 Date: Nov. 20, 1996

§ 102(e) Date: Nov. 20, 1996

[87] PCT Pub. No.: WO95/33204

PCT Pub. Date: Dec. 7, 1995

[30]  Foreign Application Priority Data

May 27, 1994  [DE]  Germany .......................... 44 18 513.8

[51] Int. Cl.⁶ .................................................. G01N 33/53
[52] U.S. Cl. ................................ 436/518; 435/5; 435/7.1; 435/7.92
[58] Field of Search .................................... 435/7.1, 7.93, 435/7.92, 5; 436/518

[56]  References Cited

U.S. PATENT DOCUMENTS 4,828,985  5/1989  Self .............................................. 435/7

OTHER PUBLICATIONS

Harlow & Lane Antibodies, A Laboratory Manual. Cold Spring Harbor Press, pp. 555–557, 1988.
Brown, J.C. & Koshland, M.E., Proc. Natl Acad Sci USA 72:5111–15, 1975.
Brown, J.C. & Koshland, M.E., Proc. Natl. Acad. Sci. USA 74:5682–86, 1977.
Barkas, T., and Watson, M.J. Immunol. 36:557–61, 1979.

Primary Examiner—Toni R. Scheiner
Attorney, Agent, or Firm—Sprung Kramer Schaefer & Briscoe

[57]  ABSTRACT

The present invention relates to an immunoassay and a method for the determination of antigens, in which an antigen is bound to a specific antibody, the conjugate formed is reacted with an immobilized capture antibody which recognizes and binds the non-bound antibody and the quantity of free or bound antibody is determined in the supernatant or on the matrix.

5 Claims, 4 Drawing Sheets

RAPID ONESIDE SINGLE TARGETING (ROST) IMMUNOASSAY METHOD

This application was filed under 35 USC 371 as the national stage of PCT/EP95/01829, which was filed May 15, 1995.

BACKGROUND OF THE INVENTION

1. Field of the Invention

The present invention relates to an immunoassay for the determination of antigens, especially high molecular weight antigens.

2. Description of the Related Art

Immunological assay systems in which monoclonal antibodies are used as the specific and selective indicator have been used for more than a decade. A large number of different methods of performing these assays have been developed and subsequently used. One essential element of immunological assay methods is the separation of the bound antigen or antibody from molecules in which no antigen-antibody reaction takes place ("bound to free separation"). In the majority of the assay systems employed this separation is carried out by immobilizing one of the assay components on a solid phase ("solid phase technology"). The immobilized molecules can consist of an antigen, an antibody or specific anchoring molecules (e.g. avidin, biotin conjugate, etc.) for the indirect fixation of immunoassay components.

The solid phase generally consists of plastics (PVC, polystyrene), latex, glass, metal or porous (filter) membranes of a wide variety of compositions. The immunoassay components (the antigen or the antibody) are then immobilized on this solid phase by adsorption or covalent binding. In the course of the incubation the bound portion of the incubation mixture (antigen-antibody complex) which is fixed to the solid phase by the immobilized assay component is removed by decanting, centrifugatiion or filtration etc.

This conventional immunoassay technique is limited by the possible variations in the biochemical or immunological properties of antigens or antibodies. Thus not all antigens can be immobilized on solid phases without undergoing changes in structure or behaviour which result in immunological (and consequently analytical) deviations from their corresponding native forms. Also it is not always possible to fix antibodies to all types of solid phase. While polyclonal antibodies can be immobilized with sufficient efficacy in almost any solid phase design, monoclonal antibodies cannot always be immobilized in satisfactory yields, or cannot be immobilized at all. The possible method of binding assay components to a solid phase by covalent bonds is also highly complicated, if at all usable for routine applications.

The by far the most widely used solid phase for immunoassay techniques, the mictrotitre plate (MTP) consisting of polystyrene, cannot always be coated with a sufficient quantity of monoclonal antibodies for effective use in assays. At present a number of methods are used in immunoassay technology for carrying out solid phase immunoassays.

In the sandwich technique at least two specific antibodies are used, for which the recovery, optimization, production and characterization of two separate antibodies is required. In addition, a comparatively complicated setup of incubation and washing stages is required. Also it is not always possible to use polystyrene MTP's for monoclonal antibodies (insufficient immobilization), but instead PVC material has to be used, or the monoclonal antibody has to be fixed indirectly by another technique (biotin/avidin etc.).

When antigens are immobilized ("half-sandwich ELISA") their structure can possibly change as a result of adsorption, thus resulting in deviations from the native molecule. Considerable optimization efforts -are still required in this area.

The problem addressed by the present invention was that of developing an immunoassay which avoids the above disadvantages.

SUMMARY OF THE INVENTION

In the following an immunoassay design for specific antibodies in particular for monoclonal antibodies is described which is distinguished by a considerably simplified assay procedure (reduction in time), a considerable shortening of the development phase (cost reduction) and an increase ion versatility (use with all types of solid phase) compared with all the known types of assay. Also the assay design described herein can be used without limitation for all fields of application (in the clinical/pharmacological fields, in veterinary medicine and for non-medical applications). The type of immunoassay described below can be designed as a qualitative and a quantitative method of detection.

The method is defined in the following as "Rapid Oneside Single Targeting" (ROST). The main features of the method are:

- only one specific, preferable monoclonal Ab (Mab, $F(ab)_2$, Fab, e.g. conjugate),
- one universal, polyclonal or monoclonal anti-Mab (e.g. rabbit anti-mouse Ig),
- only one incubation step for the bound to free separation,
- usable on all types of solid phases,
- can be designed as a qualitative and quantitative detection method,
- can be used for all antigens:
  - macromolecules,
  - particles,
  - microorganisms or cells,
  - viruses,
  - haptens.

BRIEF DESCRIPTION OF THE DRAWINGS

The invention will now be further described with reference to the drawings, wherein.

DESCRIPTION OF PREFERRED EMBODIMENTS

Figure 1:
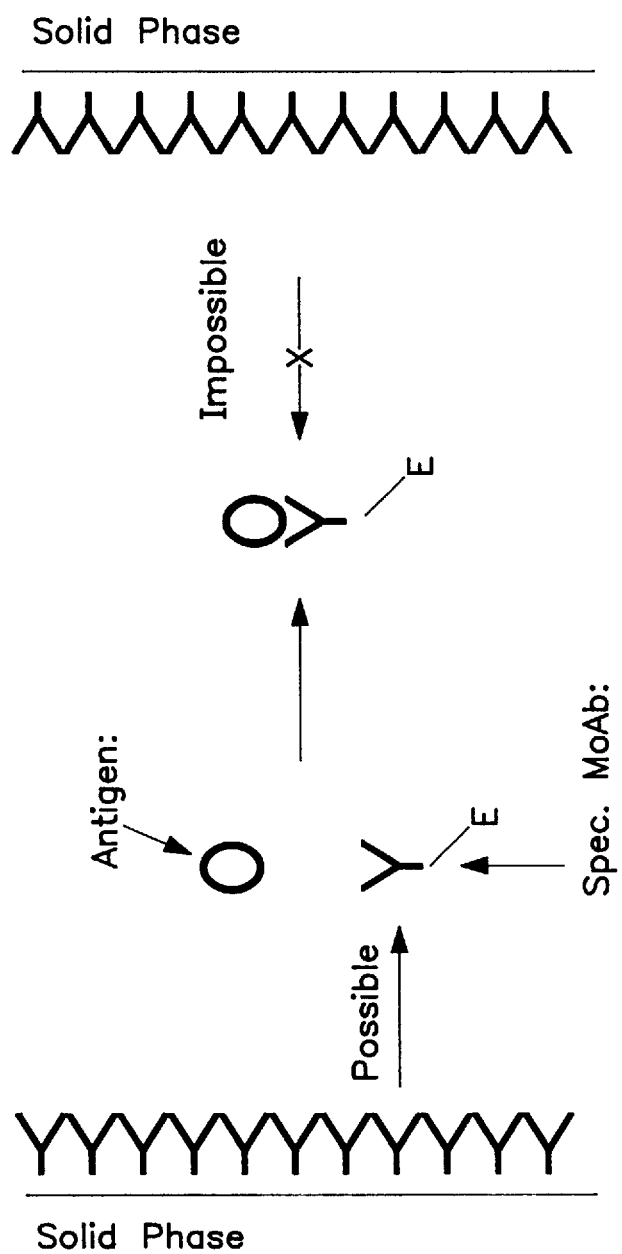
FIG. 1 is a diagram depicting the general principle by which the inventive immunoassay operates.

The method is based on the discovery that under certain conditions a polyclonal capture antibody is no longer capable of binding a specific, labeled monoclonal antibody after it has reacted with the corresponding antigen (FIG. 1).

The solid phase is coated with a commercial polyclonal double antibody (anti-mouse, anti-rat etc. as the capture antibody). The immobilization thereby obtained merely has to be optimized once for each solid phase and can also be used for all other assay methods, regardless of the antigen-antibody system involved. Capture antibodies from all types of production systems (rabbit, goat, sheep, rat, mouse etc.) can be used. The specificity of the capture antibody is of no fundamental importance (anti-Fc, anti-light chain etc.); all types of antibody can be used.

The specific immunoassay reaction is performed on solid phases which have been precoated with the capture antibody (and then after-treated as required, i.e. with a blocking agent, or by drying, etc.). The antigen (sample, standard) and the specific MAb (tracer, detectable by a marker system or by a secondary detection system) are incubated in the presence of the solid phase, during which the tracer first binds to the antigen until the binding sites present in the antigen are occupied. Any tracer not consumed by the antigen-antibody complex is bound in the second phase of the incubation (cf. FIG. 2) by the capture antibody fixed to the solid phase. After bound to free separation (e.g. by decantation from the MTP, cuvette etc. or by washing/filtration via a membrane etc.) the free tracer portion is detected by its marker system. The result of the immune reaction is inversely proportional to the antigen content.

Figure 3A:
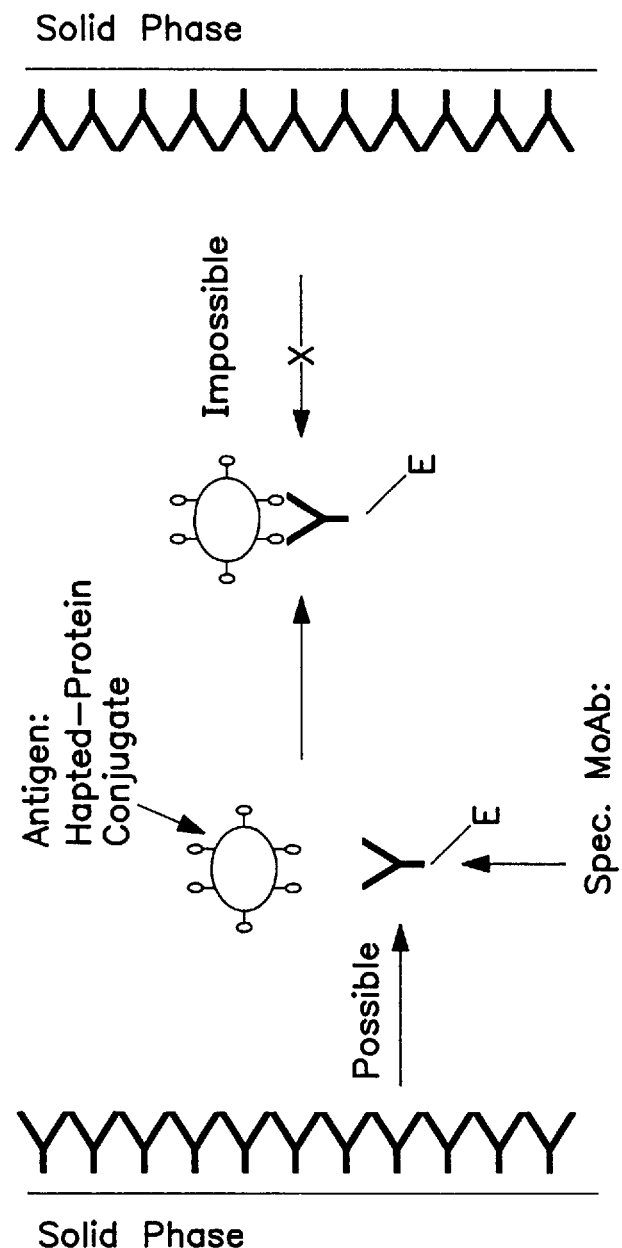
FIG. 3a is a diagram depicting the use of the inventive immunoassay to determine an antigen, which is a hapten-protein conjugate.
Figure 3B:
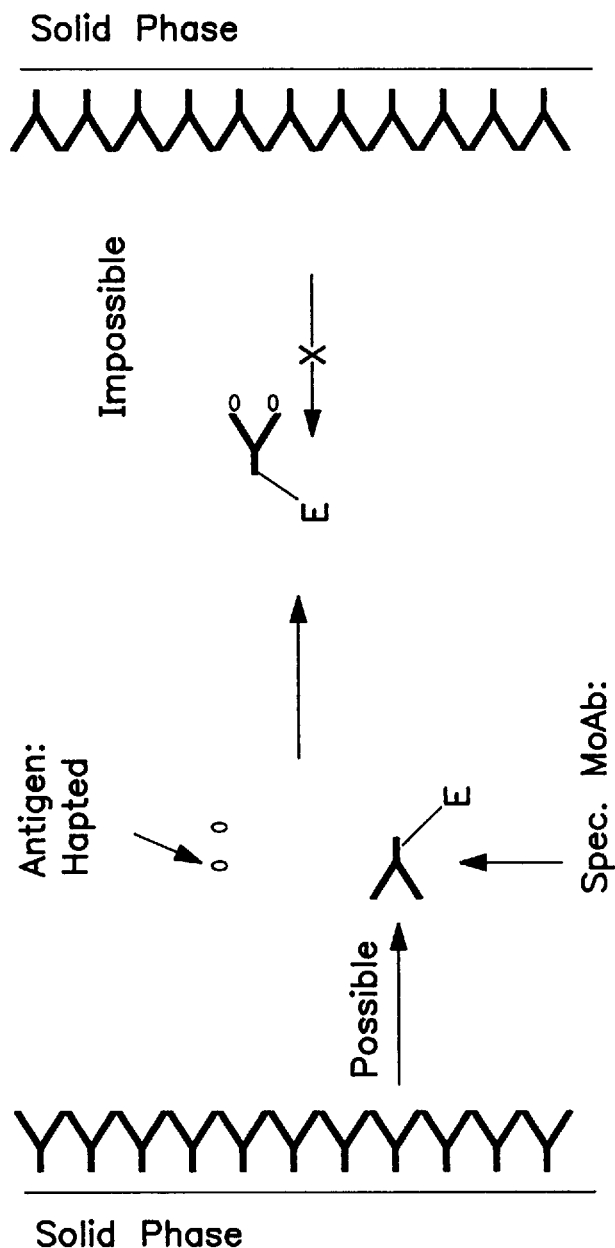
FIG. 3b is a diagram depicting the use of the inventive immunoassay to determine an antigen, which is a hapten.

The detection of low molecular weight antigens is carried out in a similar manner. An indicator antibody is however used for this purpose, which recognizes haptens as part of a conjugate or as a non-linked molecule. The corresponding capture antibody can no longer trap the antigen-specific immunoglobulin after it has formed a complex with the conjugate. In the case of non-conjugated low molecular weight antigens a capture antibody is used which recognizes the free binding site of the indicator antibody. When the low molecular weight antigen has been incorporated in the binding site of the indicator antibody this type of capture antibody can no longer trap the specific immunoglobulin. The evaluation of the immunoanalysis once again reveals inverse proportionality to the concentration of the low molecular weight antigens (cf. FIG. 3).

6 different commercial (polyclonal) immunoglobulins (from the Sigma. Co.) were used as capture antibodies. The antibodies had various specificities for the corresponding antigen (murine monoclonal antibodies). The specificities are shown in the following table:

| Sigma Cat. No. | Origin | Specificity |
| --- | --- | --- |
| M-1397 | (goat) | anti-mouse Ig, gamma chain |
| M-3014 | (goat) | anti-mouse Ig, whole molecule |
| M-4155 | (goat) | anti-mouse Ig, Fab fragment |
| M-4280 | (goat) | anti-mouse Ig, Fc fragment |
| M-8645 | (goat) | anti-mouse Ig, whole molecule |
| M-9637 | (rabbit) | anti-mouse Ig, whole molecule |

Method of incubation

Figure 2:
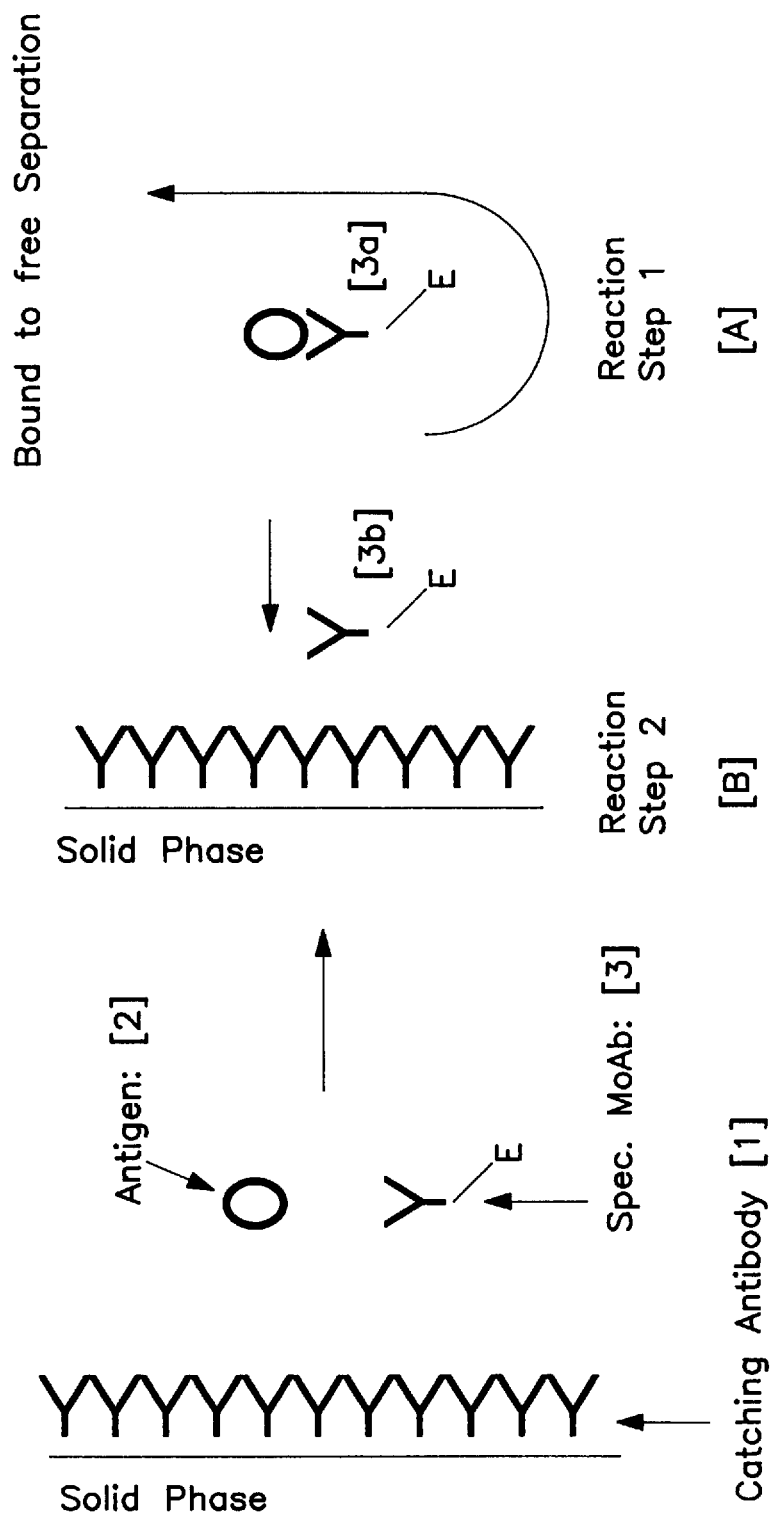
FIG. 2 is a diagram depicting the various steps of the inventive immunoassay.

On mictrotitre plates, tubules, cuvettes etc. (FIG. 2)

The incubation of the immunoassay components does not take place sequentially, as in the case of sandwich ELISA's, but simultaneously. The pretreated solid phase. (coated with the capture antibody (Harlow; E; Lane, D. Antibodies, A Laboratory Manual, Cold Spring Harbour Laboratory (1988)) is exposed to a mixture of antigen (Campbell, A. M., Monoclonal- Antibody and Immunosensor Technology, Laboratory Techniques in Biochemistry and Molecular Biology Series, Volume 23, Elsevier, Amsterdam/New York/Oxford, 1991)) and a specific, labeled (monoclonal) antibody (Tijssen, P. Practice and Theory of Enzyme Immonassays, Laboratory Techniques in Biochemistry and Molecular Biology. Series, Volume 15, Elsevier, Amsterdam/New York/Oxford, 1985)). The immune reactions which now take place, i.e. the binding of the MAb to the antigen (A) and of the capture antibody to the MAb (B) basically occur simultaneously. Reaction (B) does however not take place within the same time, due to the diffusion process required, which is problematical in the vicinity of the solid phase (wall effects).

By adding a detergent (e.g. Tween 20) the inhibition of the solid phase reaction can be additionally increased. The antigen-bound portion of the specific, labeled antibody (3a) is now no longer recognized or bound by the immobilized capture antibody (steric hindrance, change in conformation etc.). Only that portion of the detector antibody (3b) which is not bound to the antigen can still react with the capture antibodies. The bound to free separation takes place by decanting and washing prior to the addition of the enzyme substrate for the colourimetric reaction.

To perform the immunoassay according to the ROST design by the dip-stick or dot-blot technique the capture antibody was immobilized on and/or in a membrane. All conventional, commercial membranes can be used for this purpose.

For the performance of the assay the antigen and the specific, labeled antibody are combined with each other. The membrane coated with the capture antibody (in the form of a dip stick, fixed on a support) is immersed in this incubation mixture. As under the incubation conditions on the mictrotitre plate the reaction of the membrane-bound capture antibody can only take place with that portion of the conjugate (spec. MAb) which has not been consumed by an antigen-antibody complex.

Since the use of dip sticks only allows a limited number of analyses to be performed simultaneously on a practical scale, the membrane-bound ELISA according to the ROST design can also be performed in a dot blot device (BioRad, Millipore, etc.). For this purpose the membrane coated with the capture antibody is inserted into a filtration device with a microtitre plate. The sample and the conjugate can now be incubated on the membrane and filtered to separate the phases (bound to free separation). The non-consumed conjugate is detected by the marker system of the specific MAb on the membrane (e.g. by colouration).

For the performance of immunological detection methods in a filtration system (drop box) the membranes are coated with the capture antibody outside the assay device. Then the membrane segment thus pretreated is inserted into a filtration device.

The incubation of the antigen with the corresponding monoclonal detector antibody is first carried out independently and separately from the membrane of the drop box. After a short preincubation phase the reaction mixture is filtered dropwise through the membrane of the assay device, during which the reaction of the immobilised capture antibody with the non-bound portion of the indicator antibody takes place.

EXAMPLES

1. Anti-Pseu ELISA

The determination of typical antigens of the cereal pathogen Pseudocercosporella herpotrichoides was performed on various solid phases using only one monoclonal antibody. The monoclonal antibodies used were conjugated with HRP by the periodate method. The conjugate was then separated by gel permeation chromatography (Sephacryl®) and the fractions with the higher coupling rates (Ab:HRP≧3) were used for the immunological analysis.

Monoclonal antibodies from a total of 4 clones were used. Altogether 6 (commercially available) polyclonal immunoglobulins were used as capture antibodies (immobilized on a solid phase).

1.2 Assay on microtitre plates

1.2.1 Assay method

Flat-bottomed ELISA plates (MTP, Greiner, Elisa F) were coated overnight at 4° C. with various capture antibodies (Sigma) in a concentration of 1–10 μg/ml in a carbonate buffer (200 μl per well). After decanting the coating solution the MTP was after-treated with a solution of 0.01% BSA in PBS as a blocking protein (incubation with 200 μl BSA solution in PBS for 20 mins at 4° C.). After renewed decanting and washing twice with water the MTP was ready for the actual ELISA.

To perform the ELISA 100 μl of Tris buffer were first placed in each well. Then 50 μl of various dilutions of the antigen preparation (PSEU 1) in a Tris buffer were added. Finally 50 μl of the antibody-enzyme conjugates were added and the incubation mixture was thoroughly mixed (in a shaker for 1 min. at 400–500 r.p.m.).

The incubation of the mixture was carried out at 4° C. for 120 mins. Then the MTP was decanted and washed with water. The colour reaction of the marker enzyme was performed with tetramethyl benzidine (Sigma) in an acetate buffer (100 mM, pH 6.0) using hydrogen peroxide as the redox coreactant (200 μl of substrate per well). After 45 mins at room temperature the reaction was terminated by adding 50 μl of 4N sulphuric acid. The colour reaction was measured by an ELISA photometer (SLT 380AT). The measured colour signals correspond very closely to the quantities of antibody employed.

The use of a detergent, for example Tween 20, can affect the sensitivity of an ELISA based on the ROST principle.

As the concentration of the detergent increases the reaction of the wall-bound polyclonal capture antibody, which is in any case delayed, is delayed even further compared with the binding of the conjugate to the antigen. This results in increased sensitivity of the assay system.

2. Assay on a membrane in the form of a dot blot assay

2.1 Assay method

A BioRad dot blot device was used to perform the ROST ELISA on filter membranes in an MTP. The inserted filter membrane (polymer blend membrane with (+) and without (−) TMB in the layer) was coated with capture antibody M 3014. For this purpose 20 μl of a solution of the polyclonal IgG (1 mg/ml in PBS) was introduced into each well of the blot device and incubated for 30 mins at room temperature. Then the membrane was blocked with 100 μl of a 7% solution of BSA in PBS per well. The membrane was then washed with 2×250 μl of Tris buffer. The subsequent incubation of 50 μl of Pseu 1standard antigen dilution and 50 μl of conjugate SKD 0293 or SKD 0493 in Tris buffer was carried out simultaneously on the membrane segments of the blot plate for 30 minutes at room temperature. At the end of the incubation time the membrane segments were washed with 2×100 μl of Tris buffer (containing 0.1% Tween 20). The membrane was then removed from the dot blot device and immersed in the substrate mixture for 10 minutes at room temperature. Then the colouration of the membrane segments used for the immunoassay was measured by means of a reflectometer (Miles/Glukometer®3).

2.2 Results

The results show the typical path of a standard displacement curve after the incubation of a dilution series of Pseu 1 Protein.

Following the same procedure as for the immunoassay according to the ROST design on membranes with copolymerised TMB (+), assays were also performed using membranes without any incorporated addition of TMB (−). In these assays a lower assay sensitivity and a shorter dynamic range for the detection limits was found.

3. Assay on membrane dip sticks

3.1 Assay method

The immunoassay for the determination of Pseudocercosporella antigen in the form of a dip stick system was carried out on polymerblend membranes. The membrane segments were fixed to plastic supports. The dip stick with the applied membrane was immersed for 30 minutes in a solution of the capture antibody (M-3014, 1 mg/ml). After saturating the remaining immunologically relevant binding sites of the membrane (10 mins 10% BSA in PBS) the dip stick was dried on filter paper. The antigen (Pseu 1-protein) and the labeled detector antibody (Conjugate SKD 0493) were diluted in Tris buffer and combined in volumes of 100 μl. The coated test sticks were immersed in this incubation mixture and left for 30 minutes at room temperature. At the end of the incubation phase the dip stick was removed, washed in water and immersed in the substrate solution of the enzyme reaction for 10 minutes. Then the colour reaction was assessed reflectometrically in a Glukometer 3 device. In this assay there was also very high correlation between the measured results and the antibody concentration.

4. Assay on a membrane disc (drop box)

4.1 Assay method

For the performance of immunological analyses according to the ROST Design by the drop box technique the membrane discs used as the solid phase had to be coated with a capture antibody. For this purpose the membrane segments were immersed in a solution of the capture antibody for 30 minutes (1 mg/ml in PBS). Then the remaining immunologically relevant binding sites were blocked by incubating the membrane in a 7% BSA solution (PBS). After washing the membrane discs by immersion in Tris buffer they were dried in a stream of air (20° C.–30° C.). The membrane was then inserted in the drop box. The incubation of the standard dilutions of the antigen (Pseu 1) with the specific, enzyme-labeled antibody conjugate was carried out separately. 50 μl of each of the antigen dilutions and 50 μl of the conjugate were incubated together for 30 minutes at room temperature. Then the incubation mixture was passed by suction dropwise via the membrane disc coated with capture antibody into the underlying absorbent. The membrane was then washed with 2×50 μl of Tris buffer (0.1% Tween 20). After applying the substrate solution (TMB, $H_2O_2$, citrate buffer) the colouration of the membrane segments was assessed visually or by means of a reflectometer.

5. anti-meta ELISA

It was also possible to carry out the determination of specific antigens of the insect-pathogenic fungus Metarhizium anisopliae with the aid of monoclonal antibodies using an ELISA based on the ROST principle. The immunoglobulins were conjugated with HRP by the periodate method and used after purification by gel permeation chromatography.

5.1 Assay method

Flat-bottomed ELISA plates (MTP, Greiner, Elisa F) were coated overnight at 4° C. with the capture antibody M-3014 (Sigma) in a concentration of 10 μg/ml in a carbonate buffer (200 μl per well). After decanting the coating solution the MTP was. after-treated with a solution of 0.01% of BSA in PBS as a blocking protein (incubation with 200 μl of a BSA solution in PBS for 20 minutes at 4° C.) After renewed decantation and washing twice with water the MTP was ready for the actual ELISA.

For the performance of the ELISA 100 μl of Tris buffer containing 0.0001% of Tween 20 were first introduced into each well. Then 50 μl of various dilutions of the antigen preparation (META III) in Tris buffer were added. Finally 50 μl of the antibody-enzyme conjugate were added and the incubation mixture was thoroughly mixed (in a shaker for 1 minute at 400 to 500 r.p.m.). The incubation of the mixture was carried out at 4° C. for 60 minutes. Then the MTP was decanted and washed with water. The colour reaction of the marker enzyme was carried out with tetramethylbenzidine in an acetate buffer (100 mM, pH 6.0) using hydrogen peroxide as a Redox partner (200 μl of substrate per well). After 45 minutes at room temperature the reaction was terminated by adding 50 μl of 4N sulphuric acid. The colour reaction was measured in an ELISA photometer (SLT 380AT).

The results obtained produced a good standard displacement curve with a standard preparation of the META III antigen from Metarhizium anisopliae.

The ROST design for immunological analyses with monoclonal antibody conjugates showed good and reproducible results for the 8 conjugates tested and the various solid phase systems. This is true both with regard to the sensitivity and the ease of performance of the method.

6. anti-Ferritin-ELISA

Based on the ROST-principle an ELISA for determination of a protein of diagnostic value was developed. Ferritin is an important parameter for hematological analysis.

6.1 Assay method

Flat-bottom microtiterplates were coated 1 h at 37° C. with the capture antibody M-6898 (Sigma) in a concentration of 3 ug/ml in a carbonate buffer (100 ul per well). After 4× washing with PBS/0.1% Tween 20 unspecific binding sites were blocked by incubation of 3% low fat milk powder in PBS for 1 h at 20° C. After washing the antigen Ferritin and the detection antibody (H88685M, Biodesign, 3 ug/ml) were incubated simultaneously (50 ul each in 100 ul Tris/ 0.1% Tween 20) for 2 h at 4° C. Following another 4× washing the plates were incubated with a second step antibody (A-3562, Sigma, 3 ug/ml) carrying the enzyme alkaline phosphatase. After repeated washing the enzyme substrate p-Nitrophenylphosphate (PNP) was added and the colour reaction measured at 450 nm.

Using this method Ferritin in a concentration range from 50 ng/ml to 3 ug/ml could be measured.

7. ROST-Assay for use on the analyser Immuno 1

7.1 Technical standard

In clinical chemistry and immunochemistry the use of automated analysers is generally accepted for the reason of analysis time and laboratory staff reduction. For low protein analyte concentrations usually sandwich immunoassays are applied. They consist of an antibody pair (monoclonal and polyclonal) forming a sandwich with the analyte. The polyclonal antibody is conjugated to an enzyme (e.g. alkaline phosphatase) and serving as detectionantibody via catalyzing a colour reaction. The monoclonal antibody binds to the immobilization phase and thus is used as capture antibody. Depending on interference of the antibodies or other serum proteins with the analyte often a two wash protocol has to be applied for the immunoassays described above.

The aim was to simplify the method in order to accelerate the assay and to manage analyte detection with only one specific antibody.

7.2 Advantages of the ROST-technique for the Immuno 1

In this field the ROST-ELISA method offers important advantages over the commonly used sandwich technique. It allows the use of one single MAB and provides comparable specificity and sensitivity as the sandwich-ELISA. This is important in case of analytes were only small numbers of specific antibodies are available. A further advantage is the simultaneous incubation of analyte and MAB, which allows the use of one wash programms with short performance time. The ROST-technology is especially useful for high molecular weight antigens, such as ferritin. But also small analytes can be measured when they are conjugated to a carrier molecule.

7.3 Assay method

The Immuno I, produced by Miles, is a fully automated random access analyser for homogenous and heterogenous immunoassays. The Immuno 1 analyses clinical samples, such as serum or urine for estimation of drugs, hormons, proteins, and other chemicals of clinical interest. For low analyte concentrations the following sandwich methods are applied: The immobilization is usually done by FITC-labeled MAB. The FITC molecule binds to an anti-FITC antibody conjugated to magnetic particles. The polyclonal detection antibody is chemically bound to the enzyme alkaline phosphatase, which catalizes the colour reaction.

For application of the ROST-ELISA on the Immuno 1 the capture antibody must be FITC-labeled and should not be analyte specific, but recognizes the monoclonal detection antibody. Therefore only one analyte specific antibody (MAB) is necessary for the development of an assay for the Immuno 1. This is an important advantage especially for test where only small numbers of antibodies are available (e.g. Troponin I).

The introduction of the ROST-technique should be possible with the shortest assay protocol (No. 5), where all components are incubated simultaneously. The first result is available after 19 min. Sandwich-ELISA protocols often require two or three washing steps elongating the overall assay time.

Because of the reasons outlined above the ROST-ELISA-technique promises to be a valuable method, not only for the use on ELISA-plates or for dip-sticks, but also for assays on clinical immunochemical analysers.

We claim:

1. A method for the determination of the amount of an antigen, comprising:
   a) incubating said antigen and a first antibody in the presence of an immobilized second antibody, wherein said first antibody is specifically reactive with said antigen, and said second antibody is immobilized on a matrix and binds said first antibody if said first antibody is not bound to said antigen, but does not bind said first antibody if said first antibody is bound to said antigen;
   b) separating first antibody in a supernatant from first antibody bound to said second antibody immobilized on said matrix; and
   c) determining the amount of said first antibody in said supernatant or the amount of said first antibody bound to said second antibody immobilized on said matrix to give an indication of the amount of said antigen.

2. The method according to claim 1, wherein the second antibody is a polyclonal antibody.

3. The method according to claim 2, in which the polyclonal antibody is an anti-mouse antibody, an anti-rat antibody, anti-sheep or anti-goat antibody.

4. The method according to claim 1, characterized in that the antigen is a protein, a whole cell, an organelle, a virus or a hapten.

5. The method according to claim 1, wherein the first antibody is a monoclonal antibody.

* * * * *